US00RE36258E

United States Patent [19]

Coward et al.

[11] E Patent Number: Re. 36,258

[45] Reissued Date of Patent: Jul. 27, 1999

[54] LABEL HANGERS FOR BOTTLES

[75] Inventors: Roderick T. Coward; Andrew H. Whipp, both of Mississauga, Canada

[73] Assignee: CCL Label, Inc., Sioux Falls, S. Dak.

[21] Appl. No.: 08/861,235

[22] Filed: May 21, 1997

Related U.S. Patent Documents

Reissue of:

[64] Patent No.: 5,490,658
Issued: Feb. 13, 1996
Appl. No.: 08/398,362
Filed: Mar. 2, 1995

[51] Int. Cl.[6] ..... F16M 3/00

[52] U.S. Cl. ..... 248/683; 40/630; 215/399; 248/205.3; 248/311.3

[58] Field of Search ..... 248/683, 205.3, 248/311.3, 125.1; 40/310, 630, 617; 215/399

[56] References Cited

U.S. PATENT DOCUMENTS

| | | | |
|---|---|---|---|
| 2,135,236 | 11/1938 | Koppelman . | |
| 2,362,523 | 11/1944 | Armstrong et al. . | |
| 2,635,604 | 4/1953 | Fredrickson . | |
| 3,231,919 | 2/1966 | MacDonald . | |
| 3,384,258 | 5/1968 | Singier . | |
| 3,504,475 | 4/1970 | Dickard . | |
| 3,635,367 | 1/1972 | Morita et al. | 248/311.3 |
| 3,709,372 | 1/1973 | Alexander . | |
| 3,744,658 | 7/1973 | Fujio . | |
| 3,807,679 | 4/1974 | Burke et al. . | |
| 3,869,333 | 3/1975 | McMaster | 211/399 X |
| 3,884,443 | 5/1975 | McMaster | 248/467 |
| 3,893,495 | 7/1975 | Standifer . | |
| 3,908,952 | 9/1975 | Von Alven . | |
| 4,005,844 | 2/1977 | Richmond | 248/311.3 |
| 4,208,234 | 6/1980 | Lokey . | |
| 4,223,463 | 9/1980 | Good . | |
| 4,460,143 | 7/1984 | Ohama . | |
| 4,526,404 | 7/1985 | Vazquez . | |
| 4,539,766 | 9/1985 | Fast . | |
| 4,747,519 | 5/1988 | Green et al. . | |
| 4,779,367 | 10/1988 | Fast | 40/657 |
| 4,796,937 | 1/1989 | Andrea . | |
| 4,832,301 | 5/1989 | Hiramoto et al. | 248/205.3 X |
| 4,948,000 | 8/1990 | Grabenkort . | |
| 5,044,522 | 9/1991 | Roig et al. . | |
| 5,135,125 | 8/1992 | Andel et al. . | |

FOREIGN PATENT DOCUMENTS

| | | |
|---|---|---|
| 0140420 | 5/1985 | European Pat. Off. . |
| 3631021 | 9/1986 | Germany . |

*Primary Examiner*—Ramon O. Ramirez
*Attorney, Agent, or Firm*—Warner Norcross & Judd LLP

[57] ABSTRACT

A label hanger assembly has a label sheet with at least one hang strips cut therein, and in one embodiment, two hang tabs are employed The hang strip or tabs are both integral with the label sheet and engageable with a hook of an intravenous (I.V.) stand. An adhesive coating is applied to one side of the label sheet in a pattern so that the hang strip or tabs do not have adhesive on any side thereof. The label sheet adheres to the periphery of an I.V. bottle near the bottom end thereof, and the engageable portion of the hang strip or tabs engages with the hook of the I.V. stand, thereby suspending the I.V. bottle upside-down from the stand. Break-away ties hold the hang strip or tabs in place within the label sheet prior to a user pulling the hang strip or tabs out of the label sheet. A backing sheet with a release coating is provided for either one label sheet or a plurality of label sheets to be releasably mounted thereon prior to being adhered to an I.V. bottle either manually by a user or mechanically in a high-production line basis.

39 Claims, 5 Drawing Sheets

FIG. 3
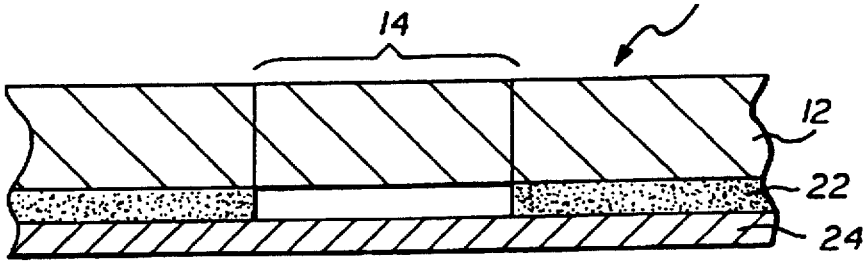
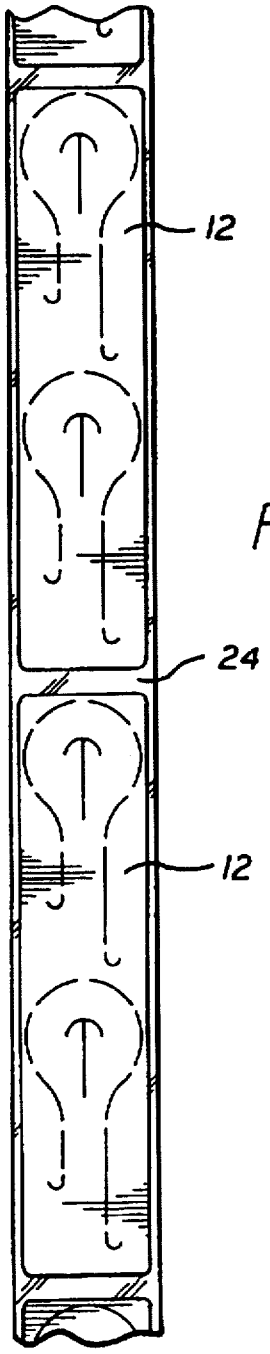
FIG. 5

FIG. 6
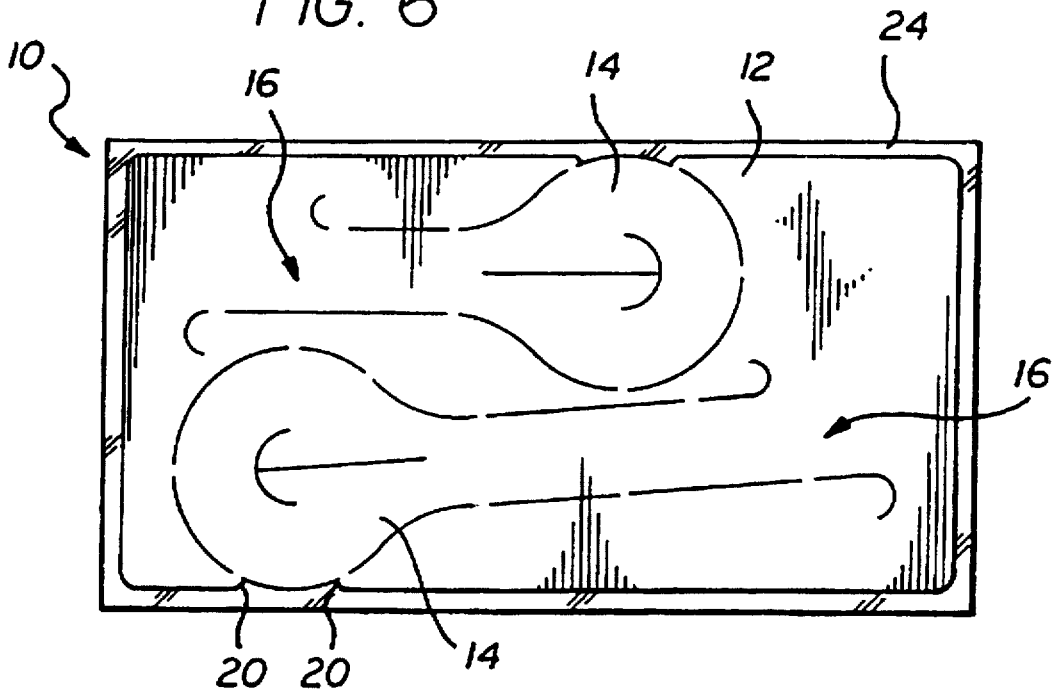
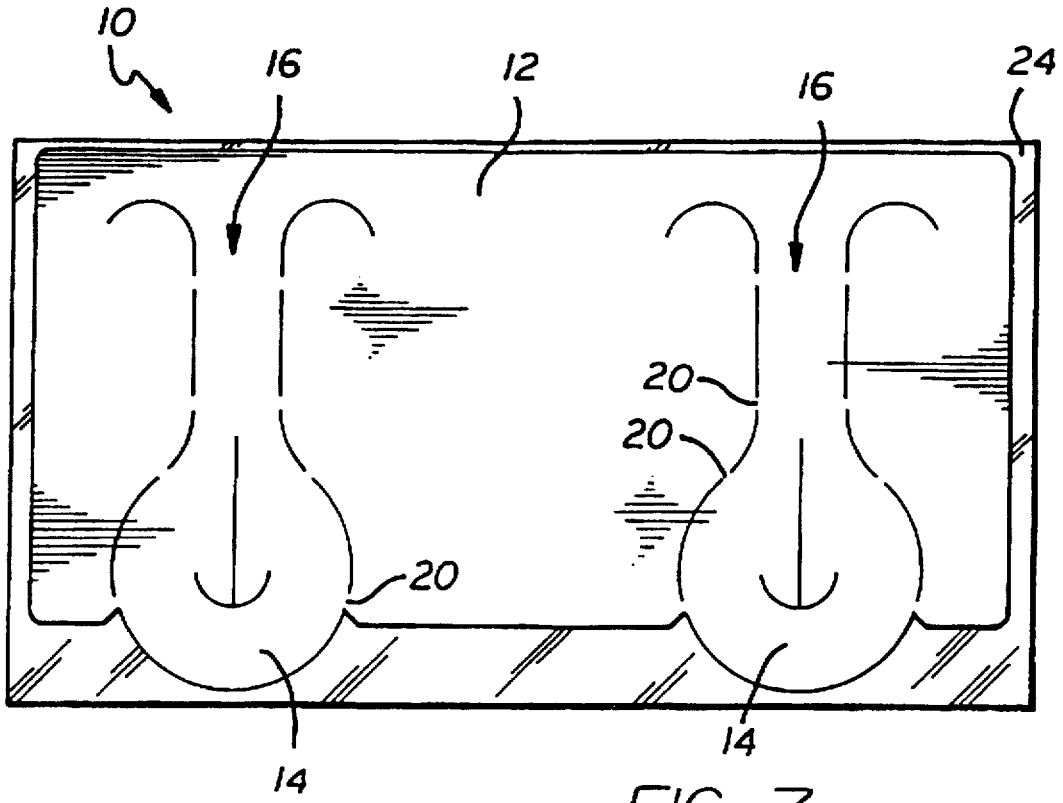
FIG. 7

LABEL HANGERS FOR BOTTLES

Matter enclosed in heavy brackets [ ] appears in the original patent but forms no part of this reissue specification; matter printed in italics indicates the additions made by reissue.

FIELD OF THE INVENTION

The present invention is related to a simplified label for suspending an intravenous bottle upside-down from a hook of an intravenous stand or dolly.

BACKGROUND OF THE INVENTION

It is well known that bottles containing pharmaceutical solutions to be administered to patients intravenously are hung invertedly or upside-down from a hook of a stand or dolly. There are many types of hangers for hanging these intravenous (I.V.) bottles from the hook of the I.V. stand. The hangers should be convenient for medical staff to use by being easily attached to the I.V. bottle and engaged with the I.V. stand. Furthermore, as much medical equipment is dispensable, the hangers should be economically manufactured so as to be reasonably priced.

One example of a hanger for an I.V. bottle is disclosed in U.S. Pat. No. 4,460,143. This hanger is attached to an I.V. bottle by means of a heat-shrinkable resin film covering the bottom periphery of the I.V. bottle, and hangs the I.V. bottle by means of a suspending ring. The requirement that heat be applied to secure the film hanger to the I.V. bottle limits the application of this hanger and reduces its ease of use. Furthermore, the relatively complicated structure requires significant processing in the manufacture thereof, so that the overall cost is relatively high.

Another example of a hanger for I.V. bottles is a plastic bag hanger as disclosed in U.S. Pat. No. 3,893,495. An I.V. bottle is received upside-down in the bag with the neck of the I.V. bottle protruding out of an opening in the bottom of the bag. The bag is then hung on an I.V. stand by means of holes in the top of the bag. Although this hanger is relatively simple to use, it requires a substantial amount of plastic film to form the bag which, except for the neck of the I.V. bottle, completely encloses the I.V. bottle.

Still another example of a hanger for an I.V. bottle is disclosed in German Patent No. 36 31 021. This hanger is comprised of a body portion with adhesive which is adhered to an I.V. bottle and a pair of tongues which extend upward from the body portion. Each tongue has a slot to receive a hook of an I.V. stand. The tongues have adhesive strips at top portions thereof which adhere together when the I.V. bottle is suspended from the stand. Because of the shape of the hanger with the tongues extending from the body portion, during the manufacture of such a hanger a significant amount of material has to be cut away and discarded or recycled to be used again. Additionally, as the body portion significantly covers most of the I.V. bottle, it uses a large amount of material. The waste and excess of material result in a relatively high cost in producing the hanger. Further, the irregular configuration of the hanger indicates that the hangers could not readily be applied to I.V. bottles on a production line basis.

U.S. Pat. No. 5,135,125 discloses yet another example of a hanger for an I.V. bottle. This hanger includes a label which is adhered to an I.V. bottle and a hanging ring which hangs on a hook of an I.V. stand. The label is a composite of a layer of adhesive, a base layer of film, a layer of ink, a layer of adhesive, another layer of ink, and an outer layer of film. The hanging ring is cut into the label and though the outer layer of film and both layers of ink with the adhesive therebetween, such that the hanging ring is comprised of these said layers. Additionally, a release lacquer or coating is applied to the base layer of film so that the hanging ring is able to be pulled free from the base layer of film and consequently the label. It is noted that the manufacturing process of this hanger is relatively complicated in the use of two label layers as well as the backing sheet.

These examples of hangers for I.V. bottles illustrate diverse approaches to hanging an I.V. bottle from a hook of an I.V. stand. To summarize, the collective group of hanger arrangements appear to be unduly complex and/or costly to apply to I.V. bottles. Therefore, there remains a need in the art of hangers for I.V. bottles for a hanger which is easily applied to an I.V. bottle and which conserves material and processing steps in the manufacture thereof.

SUMMARY OF THE INVENTION

A primary object of the present invention is to provide a label hanger for suspending an intravenous (I.V.) bottle from a hook of an I.V. stand, a label hanger which is easily applied to an I.V. bottle, either singularly or mass productively, and which is efficient in the amount of material and the processing steps required to manufacture the label hanger.

More specifically, a label hanger generally includes a label sheet having one or more hang strips or tabs die cut therein and an adhesive coating applied in a pattern on one side thereof. The hang strip or tab is integral with the label sheet at one end or both ends thereof and is engageable with a hook of an I.V. stand. Furthermore, the hang tab is held in place within the label sheet by break-away ties. The label sheet is adherent on the lower periphery of an I.V. bottle with the hang strip or tabs extending beyond the bottom end thereof a sufficient distance to engage with the hook of the stand. The label hanger may have a pair of hang tabs cut in the label sheet, in one preferred embodiment.

An important aspect of the present invention is that the adhesive coating substantially covers the side of the label sheet to which it is applied but does not cover the hang tabs; therefore, the pattern in which the adhesive coating is applied depends upon the configuration of the hang tabs, such that the hang tabs do not have any adhesive on either side thereof while the other areas of the label sheet are provided with adhesive to adhere the label to the I.V. bottle. By not having any adhesive on the hang tabs, they do not adhere to the I.V. bottle, and the engageable ends thereof are therefore able to be pulled out of and away from the label sheet, with the hang tabs pivoting or folding about the ends thereof which are integral with the rest of the label. Furthermore, the portions of the I.V. bottle which were adjacent to the hang tabs prior to the hang tabs being pulled out of the label sheet are left free of adhesive (or other material) when the I.V. bottle is suspended from the I.V. stand.

The label hangers may be mounted on a backing sheet with a release coating on one side thereof to which the label sheet is releasably adhered. Therefore, when a user is to suspend an I.V. bottle from an I.V. stand, the label sheet may be simply peeled off the backing sheet and adhered to the sides or periphery of the I.V. bottle. The engageable ends of the hang tabs are then pulled out of the label sheet and engaged with a hook of the I.V. stand. Therefore, the label hanger is easily employed in situations when a patient requires solutions to be given intravenously, be it in a hospital or a more remote location.

Moreover, by mounting a series of labels on a backing sheet or strip, the labels may be applied to I.V. bottles on a mass-produced, high-production line basis, using the usual peeling blade and label application techniques.

Further aspects of the present invention relate to the cost-saving advantages. First of all, there is efficient use of material, both in the use of plastic (or high-strength paper) material for the label sheet and in the use of adhesive material for the adhesive coating. As the label sheet may be substantially rectangular, during the manufacturing process there is no need to cut the label sheet to accommodate complicated peripheral configurations. Also, as the hang tabs may occupy a large portion of the label sheet, there is an efficient use of material with little unused space. Furthermore, the number of steps in manufacturing the label hangers and applying them to bottles are relatively few, further reducing the cost of the label hanger.

According to the present invention in yet another aspect, break-away ties are disposed between the label sheet and the hang tabs. The ties hold the hang tabs in place within the label sheet prior to a user pulling the engageable ends of the hang tabs out of and away from the label sheet, thereby breaking the ties. The ties are particularly useful in holding the hang tabs in place while the label sheet is being adhered to an I.V. bottle. The ties are easily formed during the process of die cutting the hang tabs by leaving small sections of the label sheet uncut.

Still a further aspect of the present invention are slitted eyelets formed in the engageable ends of the hang tabs. The slitted eyelets are cut into the hang tab in the form of an arrow having a rounded arrowhead, i.e., there is a transverse linear cut in the engageable end with a semicircular cut at the end thereof. By having such a configuration, the eyelets are not limited to a particular configuration of hook on which they are to be hung, e.g., cylindrical, or to a cross-sectional area of the hook. This makes the label hanger more versatile and universal in application. Furthermore, a user does not have to direct much particular attention in fitting the engageable ends onto a hook as the transverse linear cut of the eyelet allows considerable play in the hanging process.

There are a number of configurative embodiments in which the hang tabs may be cut. In one embodiment the hang tabs are mounted in substantial circumferential alignment around the lower periphery of an I.V. bottle. An alternative configuration of the hang tabs involves one of the hang tabs substantially occupying the upper portion of the label sheet and the other hang tab substantially occupying the lower portion of the label sheet, the lower hang tab having a longer length than that of the upper hang tab, so that the lengths of the portions which extend beyond the bottom of the I.V. bottle are substantially equal. Still another configurative embodiment is a "dog ear" label hanger: the hang tabs are substantially longitudinally parallel and fold up and over the bottom of the I.V. bottle.

Incidentally, although the preferable number of hang tabs is two, the present invention is suitably adaptable for one or more hang tabs cut in the label sheet for suspending I.V. bottles.

In place of the pair of hang tabs, the label hanger may have a singular hang strip cut into the label sheet. The hang strip is integral with the label sheet at the ends thereof and may be hung over a hook on an I.V. stand. Like the hang tabs, the hang strip may take on several configurative embodiments, such as a linear strip with slack-providing ends and a somewhat accordion-like layout. All embodiments afford the hang strip sufficient length to extend up and over the bottom of an I.V. bottle and to hang on a hook of an I.V. stand.

Additional advantages and novel features of the present invention will become apparent to those skilled in the art upon examination of the following detailed description and attached drawings.

BRIEF DESCRIPTION OF THE DRAWINGS

FIG. 3 is a cross-sectional view taken along line 3—3 of FIG. 1.

FIG. 5 is a top view of a plurality of label hangers mounted on a backing/sheet or strip; and FIGS. 6 and 7 are top views of label hangers with a pair of hang tabs, respectively illustrating two additional embodiments of the present invention.

DETAILED DESCRIPTION OF THE PREFERRED EMBODIMENTS

Figure 1:
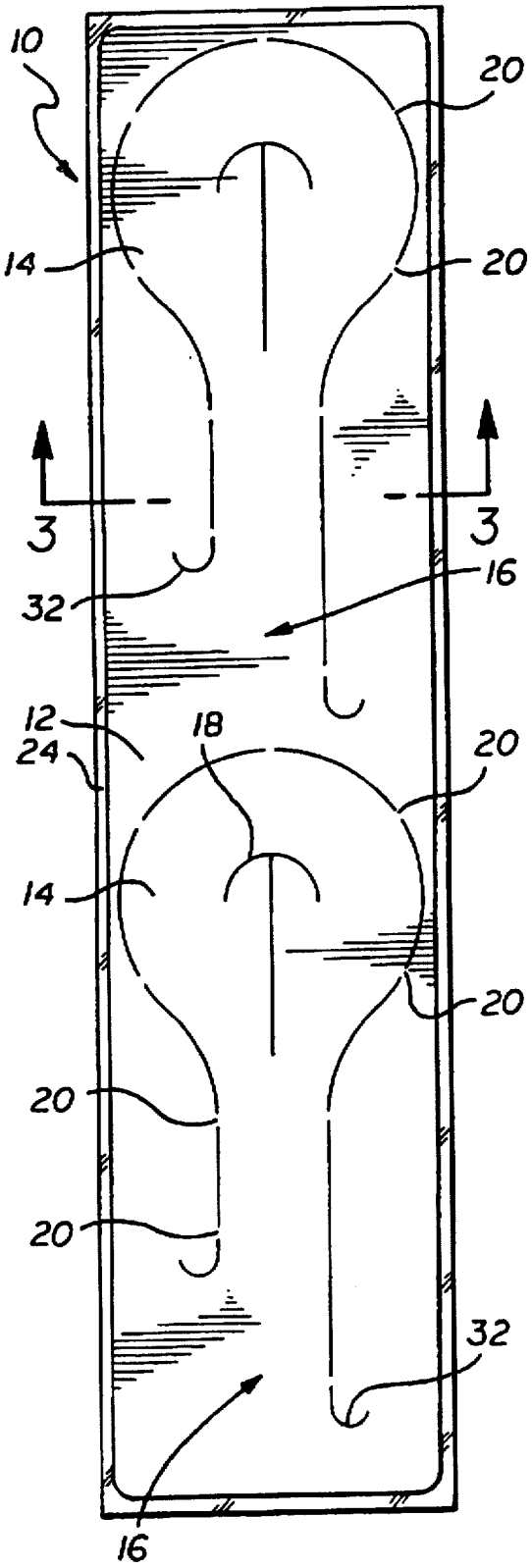
FIG. 1 is a top view of a label hanger illustrating the principle of the present invention, showing hang tabs held in place within a label sheet by ties.

Referring to FIG. 1, a preferred embodiment of a label hanger assembly 10 for suspending an intravenous (I.V.) bottle upside-down from a hook of an I.V. stand or dolly is shown. In general, one preferred embodiment of the label hanger assembly 10 includes a label sheet 12 with at least one and preferably two hang tabs 14 die cut therein. Each of the hang tabs 14 has one end which is not cut from the label sheet 12 and is therefore integral therewith, generally shown by reference numeral 16. Additionally, each of the hang tabs 14 has a slitted eyelet 18 die cut in the other end thereof which is engageable with a hook of an I.V. stand.

A plurality of break-away ties 20 may be disposed between the label sheet 12 and each of the hang tabs 14. Preferably, the ties 20 are formed during the process of cutting the hang tabs 14 into the label sheet 12 by leaving small sections of the label sheet 12 uncut; therefore, each of the ties 20 is integral with the label sheet 12 and with one of the respective hang tabs 14. The ties 20 hold the hang tabs 14 in place within the label sheet 12, and are breakable under the influence of a user pulling on the hang tabs 14. The ties 20 are particularly useful for maintaining label integrity while the labels are being adhered to I.V. bottles. It is also desirable for the ties 20 to be substantially evenly distributed around the periphery of each of the hang tabs 14.

Figure 2:
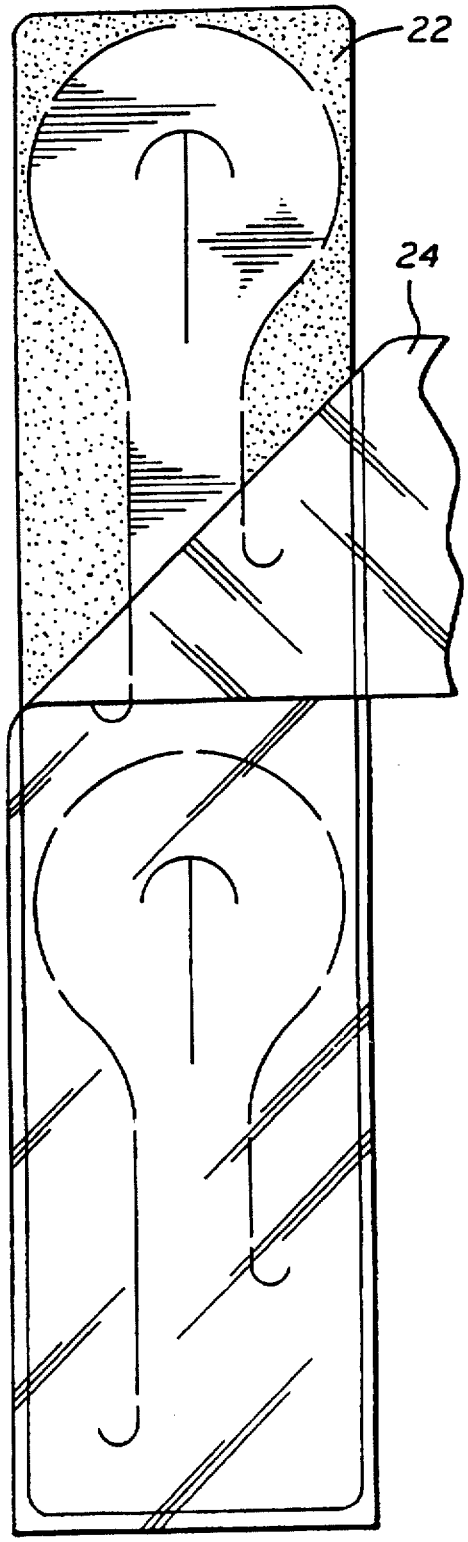
FIG. 2 is a bottom view of the label hanger of FIG. 1, showing an adhesive coating applied in a pattern and areas free of adhesive on the hang tabs.

With additional reference to FIGS. 2 and 3, the label hanger assembly 10 has an adhesive coating 22 applied to one side of the label sheet 12. As can be seen, the adhesive coating 22 is applied in a pattern to the label sheet 12, substantially covering the label sheet 12 but not covering the hang tabs 14, so that the hang tabs 14 are free of adhesive. As can be seen, the label sheet 12 is preferably an integral sheet of material, which will be discussed later.

Preferably, the adhesive coating 22 is a permanent pressure-sensitive adhesive. The nature of adhesive, whether permanent or removable, is often specified by the force required to peel (peel force) a one-inch sample strip at right angles from a stainless steel surface to which it has been adhered. The designation "permanent" is normally applied to adhesives having peel forces in the order of three pounds or more, while adhesives having a peel force of less than about two pounds are normally referred to as removable adhesive coatings.

The label hanger assembly 10 is provided with a backing sheet 24 on which the label sheet 12 with the adhesive coating 22 is releasably adherent. The backing sheet 24 has a release coating on one side thereof, abutting the adhesive coating 22, so that the label sheet 12 is releasably adhered thereto. As can be seen, the backing sheet 24 is preferably slightly perimetrically larger than the label sheet 12, thereby making it easier for a user to peel the backing sheet 24 away from the label sheet 12.

Figure 4:
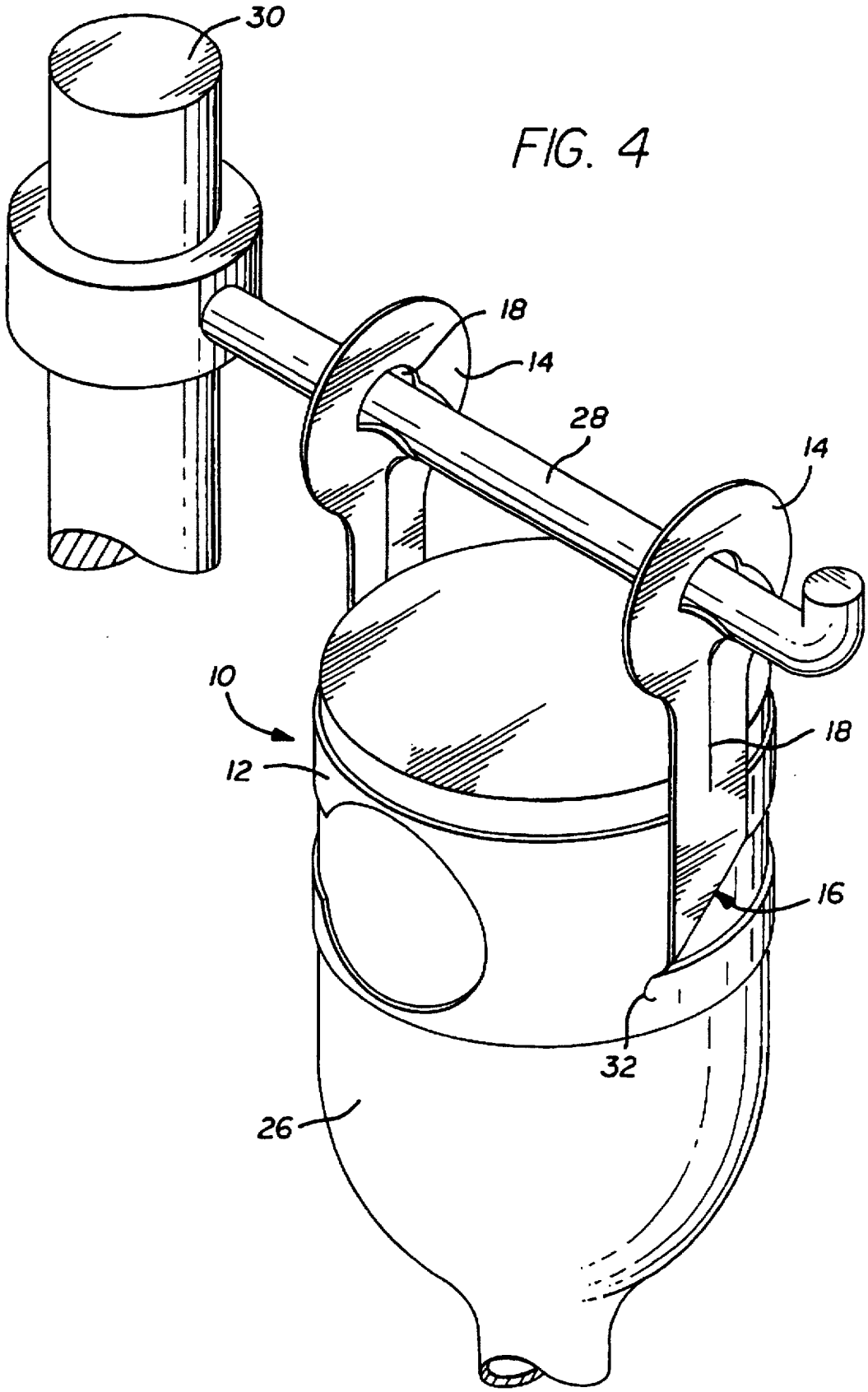
FIG. 4 is a perspective view of the label hanger adhered to an intravenous (I.V.) bottle with the hang tabs engaged with a hook an I.V. stand.

In practice, the label hanger assembly 10 is applied to an I.V. bottle 26, as shown by FIG. 4, and hung from a hook 28 of an I.V. stand 30. As can be seen, the label sheet 12 is positioned on the lower portion or periphery of the I.V. bottle 26 (i.e., the portion nearest the bottom end of the I.V. bottle 26) in a circumferential manner. While the label sheet 12 is being applied to the I.V. bottle 26, the ties 20 (not shown in FIG. 4; cf. FIG. 1) hold the hang tabs 14 in place within the label sheet 12. The ties 20 are then broken as a user pulls outwardly on the engageable ends of the hang tabs 14. The user then engages the engageable ends of the hang tabs 14 with the hook 28 by urging the eyelets 18 over the end of the hook 28, thereby suspending the I.V. bottle 26 upside-down.

As clearly shown in FIG. 4, when the hang tabs 14 are engaged with the hook 28, the I.V. bottle 26 is exposed through the label sheet 12 from where the hang tabs 14 were cut. That is, when the hang tabs 14 are lifted out of and away from the label sheet 12 by a user, there is no adhesive or other material left behind on the I.V. bottle 26.

In order to more clearly describe the present invention, the label sheet 12 is defined as having (1) a transverse axis corresponding to (or extending around) the circumference of the I.V. bottle 26 and a longitudinal axis perpendicular thereto (or extending parallel to the axis of the I.V. bottle) and (2) a top side nearer to the bottom end than to the open end of the I.V. bottle 26.

With further reference to FIG. 1, the hang tabs 14 according to the shown preferred embodiment are Substantially transversely aligned. The integral end 16 of one of the hang tabs 14 is positioned near one of the sides of the label sheet 12, and the engageable end of the same hang tab 14 is positioned toward the transverse middle of the label sheet 12. Likewise, the integral end 16 of the other hang tab 14 is positioned at or near the transverse middle of the label sheet 12, and the engageable end of the same hang tab 14 is positioned toward the other side of the label sheet 12. As can be seen, the hang tabs 14 are entirely contained within the label sheet 12, although the hang tabs 14 may intersect with the periphery of the label sheet 12, which will be discussed hereunder.

With further reference to FIG. 4, the integral ends 16 of the hang tabs 14 are preferably angled approximately 45 degrees when the label hanger assembly 10 is suspending the I.V. bottle 26. This is accomplished by cutting each of the hang tabs 14 so that the length of the bottom side thereof is longer than the respective top side thereof. More specifically, in order to achieve the preferable 45-degree angle, the length of the bottom side of each of the hang tabs 14 is substantially equal to the sum of the length of the respective top side plus the longitudinal distance between the sides, i.e., the width of the respective hang tab 14.

The 45-degree angle of the integral ends 16 distributes the force-per-unit length along the entire length of the integral side 16, not just at one point which would be the case if the top and bottom sides were the same length. By distributing the weight along the entire length of each of the integral sides 16, there is less chance of the label sheet 12 or the hang tabs 14 tearing. Furthermore, the angle eliminates slack in the top sides of the hang tabs 14 when the label hanger assembly 10 is suspending the I.V. bottle 26.

In addition to angling the integral ends 16, strain-relief cuts 32 may be cut into the label sheet 12 at the sides of the integral ends 16. The strain-relief cuts 32 are essentially continuations of the cuts that form the hang tabs 14, extending outwardly therefrom semicircularly. The strain-relief cuts 32 further distribute the weight or force-per-unit length of the I.V. bottle 26 along the integral ends 16 of the hang tabs 14, thereby reducing the strain at the junction of the integral ends 16 and the label sheet 12.

It is easily seen in FIG. 4 that the hang tabs 14 are substantially diametrically opposed. This diametric opposition provides the most stable and secure suspension of the I.V. bottle 26 by the label hanger assembly 10. In order for the hang tabs 14 to be diametrically opposed when the label sheet 12 is adhered to the I.V. bottle 26, the transverse distance between the midpoints of the integral ends 16 of the hang tabs 14 (cf. FIG. 1) is preferably and substantially equal to one-half the circumference of the I.V. bottle 26. It is notable that the label hanger assembly 10 is custom designed so as to accommodate most I.V. bottles on the market, taking into consideration circumference, weight, and so on.

With continued reference to FIGS. 1 and 4, the engageable ends of the hang tabs 14, i.e., the ends with the eyelets 18, are preferably circular in shape so that the hang tabs 14 are somewhat paddle shaped. By making the engageable ends substantially circular, the distance from the eyelets 18 to the edge of the respective hang tab 14 is greater than otherwise, thereby increasing the amount of the hang tab 14 to support the I.V. bottle 26. Furthermore, the circular engageable ends are easier to manipulate by a user when urging over the hook 28 of the I.V. stand 30.

Regarding the slitted eyelets 18, each of the eyelets 18 is substantially centered in the engageable end of the respective hang tab 14. The eyelets 18 are preferably formed by cutting a transverse cut in the longitudinal center of each of the hang tabs 14, extending substantially across the engageable end toward the transverse middle of the respective hang tab 14. In addition, a semicircular cut may be made at the end of the transverse cut which is substantially concentric with the circular edge of the respective engageable end, thereby yielding a somewhat arrow-shaped cut with a rounded arrowhead. The eyelets 18 may also simply be circular apertures cut in the engageable ends of the hang tabs 14 which are fittable over standard-sized hooks of I.V. stands. Further, the eyelits 18 can be customized with any preferred pattern or shape to meet the needs of the user.

The slitted eyelets 18 have several advantages in that they are not limited to a particular configuration of the hook 28, such as the cross section and the cross-sectional area thereof. Also, by having the eyelets 18 slitted, a user is more easily and quickly able to urge the engageable ends of the hang tabs 14 onto the hook 28 of the I.V. stand 30, an advantage which may save critical time in emergency situations when a user's attention may be distracted by other matters.

Similarly, there are advantages of having a pair of the hang tabs 14 integral with the label sheet 12. For example, if the I.V. stand 30 were an I.V. dolly, i.e., had wheels thereon, and if it were being pushed along by a user, the I.V.

bottle 26 would be swinging to and fro. And if one of the hang tabs 14 were to slide off the end of the hook 28, then there would still be the other hang tab 14 to suspend the I.V. bottle 26. This situation may be particularly pertinent during emergency situations when I.V. dollies are, for example, hurriedly pushed down the corridors of hospitals.

Specifically referencing FIG. 3, the label sheet 12 is preferably an integral sheet of material with the hang tabs 14 (only one is shown in FIG. 3) cut therethrough. The label sheet 12 may be clear or opaque and made from plastic material such as polypropylene, polyethylene, polyester, and so on, or from high-strength paper. It is noted that such material should be sufficiently strong so as not to break or tear under normal operating conditions. Commercial examples of such plastic material included Valeron, Kimdura, Tyvek, and Fabrene (all registered trade names). Furthermore, depending upon the needs of the user or the application, the label sheet 12 may be suitably laminated with additional material for added strength, abrasion resistance, chemical resistance, and so on, with such additional material also forming a part of the hang tabs 14. Additionally, graphics or text can be printed upon the label sheet 12, if desired.

In a preferential commercial embodiment of the label hanger assembly 10, the label sheet 12 may be made out of Valeron material, a high density, cross-laminated polyethylene produced by the Van Leer Company, and may have a thickness of approximately five mils to ten mils. According to tests conducted in accordance with A.S.T.M. D-882, 5.0-mil gauge Valeron, for example, has an ultimate tensile strength at break in the machine and transverse directions of 30 pounds per inch of width and 6,000 pounds per square inch of area.

Turning attention to FIG. 5, the backing sheet 24 may hold a plurality of label sheets 12. As the label hangers 10 are being manufactured, it is convenient to mount the label sheets 12 onto the backing sheet 24 substantially aligned. The backing sheet 24 may then be folded and/or perforated between the label sheets 12 for ease of transportation, storage, dispensation, and use.

Alternatively, the label sheets 12 may be mechanically mounted to I.V. bottles in a high-production line basis, using known peeling blades and label application techniques. Because of the efficiently simplistic form and construction of the label sheet 12, mass production of I.V. bottles with the label sheets 12 applied thereto is easily accomplished.

A specific commercial embodiment of the label hanger assembly 10 heretofore described and shown in FIGS. 1 and 2 may have the following approximate dimensions: the label sheet 12: a transverse width of 10 inches, a longitudinal height of 2 3/16 inches, and a thickness of 6.5 mils to 8.7 mils; each of the hang tabs 14: a longitudinal width (distance from the top to the bottom edge) of ¾ inch, a transverse length (distance from the midpoint of the integral end 16 to the engageable end) of 4 inches, a radius of the engageable end of one inch, and radius of curvature of the strain-relief cuts 32 of ⅛ inch; each of the eyelets 18: a transverse length of the transverse cut of 1 7/16 inches and a radius of curvature of the semicircular cut of 5/16 inch; the ties 20: a width of 1/64 inch, spacing therebetween on the engageable end of one inch, and spacing therebetween elsewhere of ⅞ inch to 1 3/16 inches; the adhesive coating 22: a thickness of one mil; and the backing sheet 24: from 1/16 inch to ⅛ inch larger than those dimensions of the label sheet 12 and a thickness of two mils.

Referencing FIGS. 6 and 7, further preferred embodiments of the label hanger assembly 10 in accordance with the present invention are shown. As described above, the label sheet 12 is mounted to the backing sheet 24 by the adhesive coating (not shown) which is applied in a pattern to the label sheet 12. Differentially, these preferred embodiments possess alternative configurations of the hang tabs 14. Accordingly, the adhesive coating is therefore applied in a pattern which corresponds to the alternative configurations of the hang tabs 14, so that the hang tabs 14 are free of adhesive.

Focusing attention on the preferred embodiment illustrated in FIG. 6 and taking into account the axial definitions of the label sheet 12 outlined above, one of the hang tabs 14 is substantially positioned in the upper portion of the label sheet 12, and the other hang tab 14 is substantially positioned in the lower portion of the label sheet 12. More specifically, the integral end 16 of the upper hang tab 14 is positioned near one (a first) side of the label sheet 12 while the engageable end thereof is positioned between the transverse middle and the other (a second) side of the label sheet 12, the hang tab 14 being substantially transverse. The integral end 16 of the lower hang tab 14 is positioned near the second side of the label sheet 12 while the engageable end thereof is positioned near the first side of the label sheet 12.

As can be seen from FIG. 6, the transverse length of the lower hang tab 14 is substantially equal to the sum of the transverse length of the upper hang tab 14 plus the longitudinal distance between the hang tabs 14, so that the portions of the hang tabs 14 which extend beyond the bottom end of an I.V. bottle have substantially equal lengths. This ensures that the label hanger assembly 10 evenly suspends the I.V. bottle. Furthermore, the lower hang tab 14 may be slightly angled, i.e., the integral end 16 thereof is higher than the engageable end thereof, so that the length of the lower hang tab 14 may be slightly shorter (than if it were truly transverse) while still preferentially maintaining substantially equal lengths of the portions which extend beyond the bottom of the I.V. bottle.

Furthermore, similar to the embodiment shown in FIG. 1 and accordingly described, the integral ends 16 of the hang tabs 14 are angled, so that when the hang tabs 14 fold thereabout and the engageable ends thereof engage with a hook of an I.V. stand, there is no slack in either side of each of the hang tabs 14.

Turning attention to the preferred embodiment illustrated in FIG. 7, the integral ends 16 of the hang tabs 14 are positioned near the top edge of the label sheet 12 while the engageable ends thereof are positioned in the lower portion of the label sheet 12. Preferably, the hang tabs 14 are substantially longitudinally parallel with the integral ends 16 thereof substantially transversely aligned. Further to this embodiment, the integral ends 16 are not angled as described above but are substantially transverse as the hang tabs 14 fold thereabout in a perpendicular manner, not at an angle.

Similar structures are present in the embodiments shown in FIGS. 6 and 7 that were shown in FIG. 1 and described in relation thereto. More specifically, the break-away ties 20 hold the hang tabs 14 in place within the label sheet 12 prior to a user pulling the hang tabs 14 out of and away from the label sheet 12, particularly holding the hang tabs 14 in place when the label sheet 12 is being adhered to an I.V. bottle by a user.

It is useful to note that as the hang tabs 14 may not be completely perimetrically surrounded by the label sheet 12, particularly at the engageable ends thereof (as shown in FIGS. 6 and 7), there are ties 20 disposed at or near the edge or junction of each of the hang tabs 14 and the label sheet 12, so that the hang tabs 14 do not inadvertently "flap out" of the label sheet 12 at that particular location.

Figure 8:
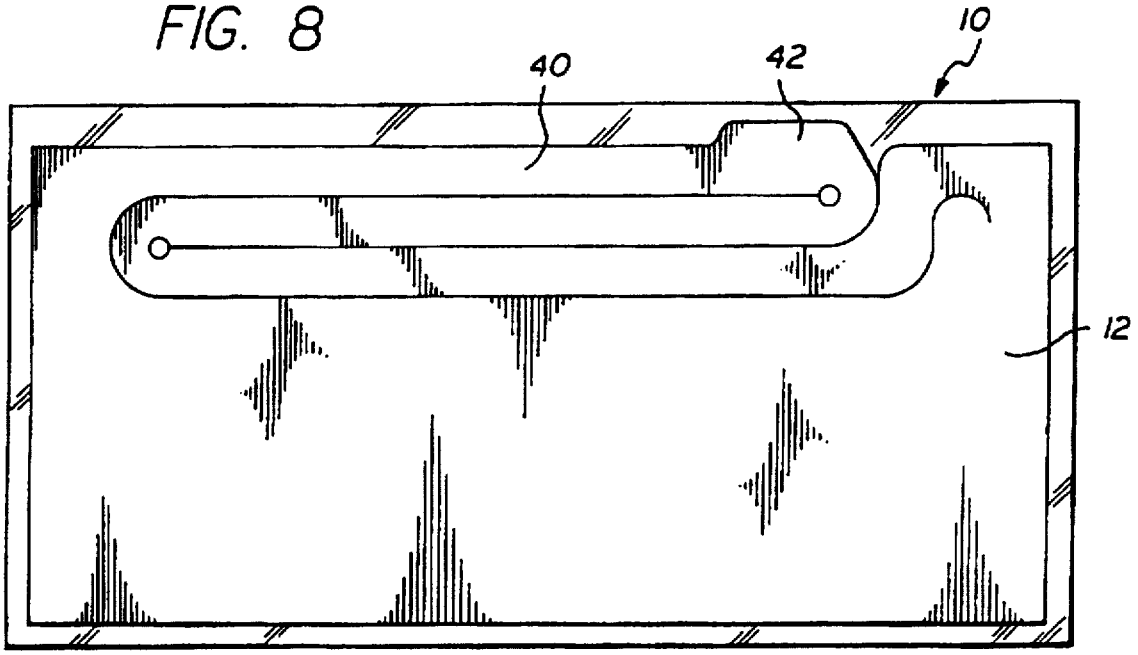
FIGS. 8 and 9 are top views of label hangers with a singular hang strip, respectively illustrating further alternative embodiments of the present invention.
Figure 9:
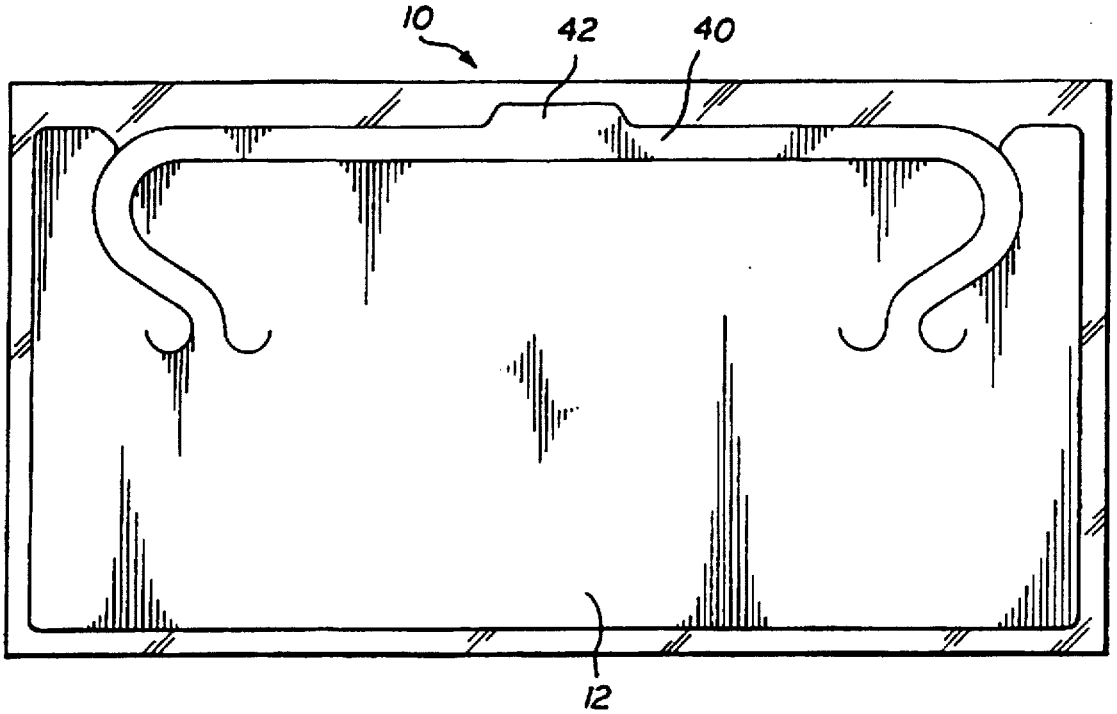

Now with reference to FIGS. 8 and 9, still further preferred embodiments of the label hanger assembly 10 in accordance with the present invention are shown. As described in the previous preferred embodiments, the label sheet 12 is mounted to the backing sheet 24 by the adhesive coating (not shown) which is applied in a pattern to the label sheet 12. The preferred embodiments shown in these figures incorporate a hang strip 40 for engaging with a hook of an I.V. stand to suspend an I.V. bottle therefrom. The hang strip 40 may have a finger tab 42 formed on an outer edge thereof to provide a user means for more easily grabbing or manipulating the hang strip 40.

Like the hang tabs 14 heretofore described, the hang strip 40 is cut from the label sheet 12 in a particular configuration with the ends thereof integral with the label sheet 12. Accordingly, the adhesive coating is applied to the label sheet 12 in a pattern which substantially covers the label sheet 12 except the area defined by the hang strip 40, such that the hang strip 40 is free of adhesive. Additionally, break-away ties are preferably formed between the hang strip 40 and the label sheet 12 to hold the hang strip 40 in place prior to engagement with an I.V. stand.

As was the case with the label hanger assembly 10 previously described, the label sheet 12 is adhered to the portion or periphery of an I.V. bottle near the bottom end thereof. The hang strip 40 has a length sufficiently long so as to extend over the bottom of I.V. bottle and to hang on a hook of an I.V. stand. Furthermore, the distance between the ends of the hang strip 40 is substantially equal to one-half the circumference of an I.V. bottle to which the label hanger assembly 10 is to be applied.

Specifically referencing FIG. 8, the hang strip 40 according to the shown preferred embodiment is essentially formed by three adjacent transverse strips. The top strip is integral with the label sheet 12 at one end thereof and with the middle strip at the other end thereof. In addition to being integral with the top strip at one end thereof, the middle strip is integral with the bottom strip at the other end thereof. Likewise, the bottom strip is integral with the label sheet 12 at the other end thereof. The hang strip 40 can also he thought of as having two 180-degree turns, thereby assuming an accordion-type arrangement It can be seen that the top edge of the hang strip 40 substantially forms the top edge of the label sheet 12 prior to adhering the label sheet 12 to an I.V. bottle.

Regarding the label hanger assembly 10 shown in FIG. 9, the hang strip 40 has a substantially transverse portion and two outwardly curving portions which provide slack in the hang strip 40, thereby providing the hang strip 40 sufficient length to extend beyond the bottom of an I.V. bottle.

In the preceding disclosure, there are shown and described a number of preferred embodiments of a label hanger for suspending I.V. bottles which are in accordance with the present invention, but as aforementioned, it is to be understood that the invention is capable of various other configurations and is capable of changes or modification within the scope of the inventive concept as expressed herein and claimed hereunder. Specifically, the dimensions and materials set forth herein are merely exemplary, and may be varied as appropriate for the size and weight of the bottle to be supported, and/or to satisfy other requirements. Furthermore, the label hanger as disclosed is not necessarily limited to I.V. bottles; it may be applied to any other object which is in need of suspension from a hook, particularly cylindrical objects.

What is claimed is:

1. A label hanger and intravenous (I.V.) bottle assembly, wherein said label hanger suspends said I.V. bottle upside-down from a hook of an I.V. stand, comprising:

an I.V. bottle;

a label sheet having a pair of hang tabs cut therein, each said hang tab being integral at one end thereof with said label sheet and engageable at the other end thereof with the hook of the I.V. stand; and an adhesive coating applied in a pattern to one side of said label sheet, said adhesive coating substantially covering all areas of said label sheet except for the areas defined by said hang tabs which are free of adhesive;

said label sheet being wrapped around said I.V. bottle and being adhered thereto by said adhesive coating;

said hang tabs having break-away ties for holding said tabs to the remainder of said label sheet as said label hanger is being applied to said I.V. bottle;

said break-away ties being integral with said label sheet but of very brief extent between said hang tabs and the remainder of said label sheet; and the area of said I.V. bottle beneath said hang tabs being free of adhesive both before and after said ties are broken and said hang tabs are extended to engage with the hook of the I.V. stand.

2. A label hanger assembly for suspending an intravenous (I.V.) bottle upside-down from a hook of an I.V. stand, comprising:

a label sheet;

a hang strip cut from said label sheet, said hang strip being integral at both ends thereof with said label sheet, and said hang strip being removable out of and away from said label sheet and having a sufficient length to clear the bottom of an I.V. bottle and to engage with a hook of an I.V. stand;

a plurality of breakable ties disposed between said label sheet and said hang strip, said ties securing said hang strip within said label sheet prior to a user pulling said hang strip out of said label sheet;

an adhesive coating applied in a pattern to one side of said label sheet, said adhesive coating substantially covering said label sheet except for the area defined by said hang strip, so that said hang strip is free of adhesive;

said label sheet adherent to an I.V. bottle by said adhesive coating and defined as having a top edge positioned nearer to the bottom end than to the open end and a bottom edge positioned nearer to the open end than to the bottom end of the I.V. bottle;

said label sheet having a transverse axis defined as extending around the circumference and a longitudinal axis defined as extending parallel to the axis of the I.V. bottle;

the ends of said hang strip respectively positioned near the sides of said label sheet, said hang strip having two approximately 180-degree turns; and said hang strip having an upper portion, a middle portion, and a lower portion, the ends of said middle portion being integral with a respective end of said upper and said lower portion at said 180-degree turns, said portions being substantially transverse.

3. A label hanger for suspending an intravenous (I.V.) bottle upside-down from a hook of an I.V. dolly or stand, comprising:

a label sheet having a pair of hang strips cut therefrom and an adhesive coating applied thereon, said label sheet being adherent to an I.V. bottle;

each said hang strip having one end thereof integral with said label sheet and the other end thereof removable out of and away from said label sheet and engageable with a hook of an I.V stand;

each said hang strip having a plurality of breakable ties for securing said hang tab to said label sheet prior to a user pulling said engageable end thereof out of said label sheet;

said adhesive coating applied in a pattern to one side of said label sheet, substantially covering said label sheet except for the area defined by said hang strips, so that said hang strips are free of adhesive;

said label sheet having a top edge positioned nearer to the bottom end than to the open end and a bottom edge positioned nearer to the open end than to the bottom end of an I.V. bottle when adhered thereto;

said label sheet having a transverse axis corresponding with the circumference and a longitudinal axis corresponding with the height of an I.V. bottle when adhered thereto, said label sheet having a transverse middle;

each said hang strip folding along said integral end thereof and extending beyond the bottom end of an I.V. bottle a sufficient distance to enable said engageable ends to engage with a hook of an I.V. stand;

said integral end of one of said hang strips positioned near a first side of said label sheet, and said engageable end of the same said hang strip positioned between said transverse middle and a second side of said label sheet, said hang strip being positioned in substantially the top half of said label sheet;

said integral end of the other said hang strip positioned near said second side of said label sheet, and said engageable end of the same said hang strip positioned near said first side of said label sheet, said hang strip being positioned in substantially the bottom half of said label sheet; and the transverse length of said hang strip positioned in the bottom half of said label sheet substantially equal to the sum of the transverse length the other said hang strip plus the longitudinal distance between said hang strips, whereby the respective portions of said hang strips which extend beyond the bottom of the I.V. bottle have substantially equal lengths.

4. A label hanger assembly for suspending an intravenous (I.V.) bottle upside-down from a hook of an I.V. stand, comprising:

a label sheet;

a hang strip cut from said label sheet, said hang strip being integral at both ends thereof with said label sheet, and said hang strip being removable out of and away from said label sheet and having a sufficient length to clear the bottom of an I.V. bottle and to engage with a hook of an I.V. stand, said hang strip having a middle portion;

a plurality of breakable ties disposed between said label sheet and said hang strip, said ties securing said hang strip within said label sheet prior to a user pulling said hang strip out of said label sheet;

an adhesive coating applied in a pattern to one side of said label sheet, said adhesive coating substantially covering said label sheet except for the area defined by said hang strip, so that said hang strip is free of adhesive;

said label sheet adherent to an I.V. bottle by said adhesive coating and defined as having a top edge positioned nearer to the bottom end than to the open end and a bottom edge positioned nearer to the open end than to the bottom end of the I.V. bottle;

said label sheet having a transverse axis defined as extending around the circumference and a longitudinal axis defined as extending parallel to the axis of the I.V. bottle, said label sheet having a longitudinal middle portion;

the ends of said hang strip positioned substantially in said longitudinal middle portion of said label sheet, and said middle portion of said hang strip positioned in the upper portion of said label sheet; and said hang strip curving transversely outwardly and upwardly from the ends thereof to said middle portion thereof, so that the length of said hang strip is sufficiently long to allow the middle portion of the hang strip to extend over the bottom of an I.V. bottle to engage with a hook thereof.

5. A label hanger for suspending an intravenous (I.V.) bottle upside-down from a hook of an I.V. dolly or stand, comprising:

a label sheet having at least one hang strip cut therefrom and an adhesive coating applied thereon, said label sheet being adherent to an I.V. bottle;

said hang strip having at least one end thereof integral with said label sheet, and the remainder of said hang strip being removable out of and away from said label sheet and engageable with a hook of an I.V. stand;

said hang strip having a plurality of breakable ties for securing said hang strip to said label sheet prior to a user pulling the remainder of said strip out of said label sheet; and said adhesive coating being applied in a pattern to one side of said label sheet, substantially covering said label sheet except for the area defined by said hang strip, so that said hang strip is free of adhesive.

6. A label hanger as claimed in claim 5, wherein said ties are integral with said hang strip and said label sheet.

7. A label hanger as claimed in claim 5, wherein said label sheet is releasably adherent on a backing sheet having a release coating on one side thereof prior to being adhered to an I.V. bottle.

8. A label hanger as claimed in claim 7, wherein said backing sheet accommodates a plurality of said label sheets.

9. A label hanger as claimed in claim 5, wherein:

said hang strip has two ends, each said end being integral with said label sheet;

said hang strip being removable out of and away from said label sheet and having a sufficient length to clear the bottom of an I.V. bottle and to engage with a hook of an I.V. stand.

10. A label hanger as claimed in claim 5, wherein there are a pair of said hang strips cut from said label sheet;

each said hang strip having one end thereof integral with said label sheet and the other end thereof engageable with a hook of an I.V. stand;

said label sheet having a top edge positioned nearer to the bottom end than to the open end and a bottom edge positioned nearer to the open end than to the bottom end of an I.V. bottle when adhered thereto;

said label sheet having a transverse axis corresponding with the circumference and a longitudinal axis corresponding with the height of an I.V. bottle when adhered thereto; and each said hang strip folding along said integral end thereof and extending beyond the bottom end of an I.V.

bottle a sufficient distance to enable said engageable ends to engage with a hook of an I.V. stand.

11. A label hanger as claimed in claim 10, wherein said integral ends of said hang strips are positioned near said top edge of said label sheet and said engageable ends of said hang strips are positioned toward said bottom edge of said label sheet, so that said hang strips are substantially longitudinal.

12. A label hanger and intravenous (I.V.) bottle assembly, wherein said label hanger suspends said I.V. bottle upside-down from a hook of an I.V. stand, comprising:

an I.V. bottle;

a label sheet having a pair of hang tabs cut therein, each said hang tab being integral at one end thereof with said label sheet and engageable at the other end thereof with the hook of the I.V. stand; and an adhesive coating applied in a pattern to one side of said label sheet, said adhesive coating substantially covering all areas of said label sheet except for the areas defined by said hang tabs which are free of adhesive;

the area of said I.V. bottle beneath said ties free of adhesive both before and after said ties are broken and said hang tabs are extended to engage with the hook of the I.V. stand;

said label sheet being wrapped around said I.V. bottle and being adhered thereto by said adhesive coating;

said label sheet being substantially rectangular, having a transverse axis corresponding with the circumference of said I.V. bottle, and having a transverse middle;

said integral end of one of said hang tabs positioned near one of the sides of said label sheet, and said engageable end of the same said hang tab positioned toward said transverse middle of said label sheet;

said integral end of the other said hang tab positioned at or near said transverse middle of said label sheet, and said engageable end of the same said hang tab positioned toward the other side of said label sheet; and said hang tabs having break-away ties for holding said tabs to the remainder of said label sheet as said label hanger is being applied to said I.V. bottle.

13. A label hanger and I.V. bottle assembly as claimed in claim 12, wherein:

each said hang tab has a top edge and a bottom edge, said top edges being nearer to the bottom end of said I.V. bottle and farther from the open end of said I.V. bottle than respective said bottom edges when said label assembly is adhered to said I.V. bottle, said top edges being shorter in length than respective said bottom edges by a distance substantially equal to the distance between said edges; and each said integral end respectively extending between said top edge and said bottom edge;

whereby when said hang tabs are extended and said engageable ends thereof are engaged with a hook of an I.V. stand, said integral ends are angled with respect to the transverse axis of said label sheet by approximately 45 degrees.

14. A label hanger and I.V. bottle assembly as claimed in claim 12, wherein said adhesive coating is a permanent pressure-sensitive adhesive.

15. A label hanger assembly for suspending an intravenous (I.V.) bottle upside-down from a hook of an I.V. stand, comprising:

a label sheet;

a hang strip cut from said label sheet, said hang strip being integral at both ends thereof with said label sheet, and said hang strip being removable out of and away from said label sheet and having a sufficient length to clear the bottom of an I.V. bottle and to engage with a hook of an I.V. stand;

a plurality of breakable ties disposed between said label sheet and said hang strip, said ties securing said hang strip within said label sheet prior to a user pulling said hang strip out of said label sheet;

an adhesive coating applied in a pattern to one side of said label sheet, said adhesive coating substantially covering said label sheet except for the area defined by said hang strip, so that said hang strip is free of adhesive;

said label sheet being adherent to an I.V. bottle by said adhesive coating and defined as having a top edge positioned nearer to the bottom end than to the open end and a bottom edge positioned nearer to the open end than to the bottom end of the I.V. bottle; and said label sheet having a transverse axis defined as extending around the circumference and a longitudinal axis defined as extending parallel to the axis of the I.V. bottle.

16. The label hanger assembly as claimed in claim 15, further comprising a backing sheet having a release coating on one side thereof, said label sheet with said adhesive coating being releasably adherent to said backing sheet prior to being adhered to an I.V. bottle.

17. The label hanger assembly as claimed in claim 15, further comprising a backing strip having a release coating on one side thereof, said backing strip receiving a plurality of said label sheets with said adhesive coating;

said label sheet being releasably adherent on said backing sheet prior to being adhered to an I.V. bottle.

18. A label hanger for suspending an intravenous (I.V.) bottle upside-down from a hook of an I.V. dolly or stand, comprising:

a label sheet having a pair of hang tabs cut therefrom and an adhesive coating applied thereon, said label sheet being adherent to an I.V. bottle;

each said hang strip having one end thereof integral with said label sheet and the other end thereof removable out of and away from said label sheet and engageable with a hook of an I.V. stand;

each said hang strip having a plurality of breakable ties for securing said hang tab to said label sheet prior to a user pulling said engageable end thereof out of said label sheet;

said adhesive coating applied in a pattern to one side or said label sheet, substantially covering said label sheet except for the area defined by said hang strips, so that said hang strips are free of adhesive;

said label sheet having a top edge positioned nearer to the bottom end than to the open end and a bottom edge positioned nearer to the open end than to the bottom end of an I.V. bottle when adhered thereto;

said label sheet having a transverse axis corresponding with the circumference and a longitudinal axis corresponding with the height of an I.V. bottle when adhered thereto, said label sheet having a transverse middle;

each said hang strip folding along said integral end thereof and extending beyond the bottom end of an I.V. bottle a sufficient distance to enable said engageable ends to engage with a hook of an I.V. stand;

said integral end of one of said hang strips positioned near one of the sides of said label sheet, and said engageable end of the same said hang strip positioned toward said transverse middle of said label sheet; and said integral end of the other said hang strip positioned at or near said transverse middle of said label sheet, and said engageable end of the same said hang strip positioned toward the other side of said label sheet.

19. A label hanger as claimed in claim 18, wherein each said hang strip has a top edge and a bottom edge;

said top edges nearer to the bottom end of an I.V. bottle and farther from the open end of the I.V. bottle than respective said bottom edges when said label assembly is adhered to the I.V. bottle;

said top edges shorter in length than respective said bottom edges by a distance substantially equal to the distance between said edges; and each said integral end respectively extending between said top edge and said bottom edge;

whereby when said hang strips are extended and said engageable ends thereof are engaged with a hook of an I.V. stand, said integral ends are angled with respect to said transverse axis of said label sheet by approximately 45 degrees.

20. A label and backing sheet assembly for the application of hang tab type labels to intravenous bottles, comprising:

a backing strip layer coated with a release coating;

a label layer overlying said backing strip layer;

said label layer including a plurality of spaced individual labels, each said label including at least one die cut hang strip having ties holding said hang strip in place on said label;

pressure sensitive adhesive between each said label and said backing strip layer in the areas of said label other than said hang strip; and the self-sustaining layers of said assembly consisting solely of said backing strip layer and said label layer;

whereby when said labels are applied to an intravenous bottle, said hang strips may be partly pulled loose from the balance of said label by breaking said ties, with the bottle being exposed in each area where a hang tab is pulled away from the bottle, and said hang strips permitting support of the bottle from said hang strips, with the bottle inverted.

*21. A label hanger and container assembly comprising:*

*a container;*

*a label sheet having at least one hang tab cut therein, said hang tab being integral at one end thereof with said label sheet and engageable at the other end thereof with a hook;*

*an adhesive coating applied in a pattern to one side of said label sheets said adhesive coating substantially covering all areas of said label sheet except for the areas defined by said hang tab which is free of adhesive;*

*said label sheet being wrapped around said container and being adhered thereto by said adhesive coating;*

*said hang tab having break-away ties for holding said tab to the remainder of said label sheet as said label hanger is being applied to said container;*

*said break-away ties being integral with said label sheet but of very brief extent between said hang tab and the remainder of said label sheet; and*

*the area of said container beneath said hang tab being free of adhesive both before and after said ties are broken and said hang tab is extended to engage with the hook.*

*22. A label hanger and container assembly as claimed in claim 21 wherein said label sheet includes at least two hang tabs.*

*23. A label hanger assembly for suspending a container comprising:*

*a label sheet;*

*a hang strip cut from said label sheet, said hang strip being integral at both ends thereof with said label sheet, and said hang strip being removable out of and away from said label sheet and having a sufficient length to clear the bottom of a container and to engage with a hook;*

*a plurality of breakable ties disposed between said label sheet and said hang strip, said ties securing said hang strip within said label sheet prior to a user pulling said hang strip out of said label sheet;*

*an adhesive coating applied in a pattern to one side of said label sheet, said adhesive coating substantially covering said label sheet except for the area defined by said hang strip, so that said hang strip is free of adhesive;*

*said label sheet adherent to a container by said adhesive coating and defined as having a top edge positioned nearer to the bottom end than to the open end and a bottom edge positioned nearer to the open end than to the bottom end of the container;*

*said label sheet having a transverse axis defined as extending around the circumference and a longitudinal axis defined as extending parallel to the axis of the container;*

*the ends of said hang strip respectively positioned near the sides of said label sheet, said hang strip having two approximately 180-degree turns; and*

*said hang strip having an tipper portion, a middle portion, and a lower portion, the ends of said middle portion being integral with a respective end of said tipper and said lower portion at said 180-degree turns said portions being substantially transverse.*

*24. A label hanger assembly for suspending a container comprising:*

*a label sheet;*

*a hang strip cut from said label sheet said hang strip being integral at both ends thereof with said label sheet, said hang strip being removable out of and away from said label sheet and having a sufficient length to clear the bottom of a container and to engage with a hook, said hang strip having a middle portion;*

*a plurality of breakable ties disposed between said label sheet and said hang strip, said ties section said hang strip within said label sheet prior to a user pulling said hang strip out of said label sheet;*

*an adhesive coating applied in a pattern to one side of said label sheet, said adhesive coating substantially covering said label sheet except for the area defined by said hang strip, so that said hang strip is free of adhesive;*

*said label sheet adherent to a container by said adhesive coating and defined as having a top edge positioned nearer to the bottom end than to the open end and a bottom edge positioned nearer to the open end than to the bottom end of the container;*

*said label sheet having a transverse axis defined as extending around the circumference and a longitudinal axis defined as extending parallel to the axis of the container, said label sheet having a longitudinal middle portion;*

*the ends of said hang strip positioned substantially in said longitudinal middle portion of said label sheet, said*

*middle portion of said hang strip positioned in the upper portion of said label sheet; and*

*said hang strip curving transversely outwardly and upwardly from the ends thereof to said middle portion thereof, so that the length of said hang strip is sufficiently long to allow the middle portion of the hang strip to extend over the bottom of a container to engage with a hook.*

*25. A label hanger for suspending a container comprising:*

*a label sheet having at least one hang strip cut therefrom and an adhesive coating applied thereon, said label sheet being adherent to a container;*

*said hang strip having at least one end thereof integral with said label sheet, and the remainder of said hang strip being removable out of and away from said label sheet and engageable with a hook;*

*said hang strip having a plurality of breakable ties for securing said hang strip to said label sheet prior to a user pulling the remainder of said strip out of said label sheet; and*

*said adhesive coating being applied in a pattern to one side of said label sheet, substantially covering said label sheet except for the area defined by said hang strip, so that said hang strip is free of adhesive.*

*26. A label hanger as claimed in claim 25 wherein said ties are integral with said hang strip and said label sheet.*

*27. A label hanger as claimed in claim 25 wherein said label sheet is releasably adherent on a backing sheet having a release coating on one side thereof prior to being adhered to a container.*

*28. A label hanger as claimed in claim 27 wherein said backing sheet accommodates a plurality of said label sheets.*

*29. A label hanger as claimed in claim 25 wherein:*

*said hang strip has two ends, each said end being integral with said label sheet,*

*said hang strip being removable out of and away from said label sheet and having a sufficient length to clear the bottom of a container and to engage with a hook.*

*30. A label hanger as claimed in claim 25, wherein there are a pair of said hang strips cut from said label sheet;*

*each said hang strip having one end thereof integral with said label sheet and the other end thereof engageable with a hook;*

*said label sheet having a top edge positioned nearer to the bottom end than to the open end and a bottom edge positioned nearer to the open end than to the bottom end of a container when adhered thereto;*

*said label sheet having a transverse axis corresponding with the circumference and a longitudinal axis corresponding with the height of a container when adhered thereto; and*

*each said strip folding along said integral end thereof and extending beyond the bottom end of a container a sufficient distance to enable said engageable ends to engage with a hook.*

*31. A label hanger as claimed in claim 30 wherein said integral ends of said hang strips are positioned near said top edge of said label sheet and said engageable ends of said hang strips are positioned toward said bottom edge of said label sheet, so that said hang strips are substantially longitudinal.*

*32. A label hanger and container assembly comprising:*

*a container;*

*a label sheet having a pair of hang tabs cut therein, each said hang tab being integral at one end thereof with said label sheet and engageable at the other end thereof with the hook; and*

*an adhesive coating applied in a pattern to one side of said label sheet, said adhesive coating substantially covering all areas of said label sheet except for the areas defined by said hang tabs which are free of adhesive;*

*the area of said container beneath said ties free of adhesive both before and after said ties are broken and said hang tabs are extended to engage with the hook;*

*said label sheet being wrapped around said container and being adhered thereto by said adhesive coating;*

*said label sheet being substantially rectangular, having a transverse axis corresponding with the circumference of said container, and having a transverse middle;*

*said integral end of one of said hang tabs positioned near one of the sides of said label sheet, and said engageable end of the same said hang tab positioned toward said transverse middle of said label sheet;*

*said integral end of the other said hang tab positioned at or near said transverse middle of said label sheet, and said engageable end of the same said hang tab positioned toward the other side of said label sheet; and*

*said hang tabs having break-away ties for holding said tabs to the remainder of said label sheet as said label hanger is being applied to said container.*

*33. A label hanger and container assembly as claimed in claim 32 wherein:*

*each said hang tab has a top edge and a bottom edge, said top edges being nearer to the bottom end of said container and farther from the open end of said container than respective said bottom edges when said label assembly is adhered to said container, said top edges being shorter in length than respective said bottom edges by a distance substantially equal to the distance between said edges; and*

*each said integral end respectively extending between said top edge and said bottom edge;*

*whereby when said hang tabs are extended and said engageable ends thereof are engaged with a hook, said integral ends are angled with respect to the transverse axis of said label sheet by approximately 45 degrees.*

*34. A label hanger assembly for suspending a container comprising:*

*a label sheet;*

*a hang strip cut from said label sheet, said hang strip being integral at both ends thereof with said label sheet, and said hang strip being removable out of and away from said label sheet and having a sufficient length to clear the bottom of a container and to engage with a hook;*

*a plurality of breakable ties disposed between said label sheet and said hang strip, said ties securing said hang strip within said label sheet prior to a user pulling said hang strip out of said label sheet;*

*an adhesive coating applied in a pattern to one side of said label sheet, said adhesive coating substantially covering said label sheet except for the area defined by said hang strip, so that said hang strip is free of adhesive; and*

*said label sheet being adherent to a container by said adhesive coating and defined as having a top edge positioned nearer to the bottom end than to the open end and a bottom edge positioned nearer to the open end than to the bottom end of the container.*

*35. A label hanger assembly as claimed in claim 34 further comprising a backing sheet having a release coating on one side thereof, said label sheet with said adhesive coating being releasably adherent to said backing sheet prior to being adhered to a container.*

*36. A label hanger assembly as claimed in claim 34 further comprising a backing sheet having a release coating on one side thereof, said backing sheet receiving a plurality of said label sheets with said adhesive coating;*

*each of said label sheets being releasably adherent on said backing sheet prior to being adhered to a container.*

*37. A label hanger for suspending a container comprising:*

*a label sheet having a pair of hang strips cut therefrom and an adhesive coating applied thereon, said label sheet being adherent to a container;*

*each said hang strip having one end thereof integral with said label sheet and the other end thereof removable out of and away from said label sheet and engageable with a hook;*

*each said hang strip having a plurality of breakable ties for securing said hang strip to said label sheet prior to a user pulling said engageable end thereof out of said label sheet;*

*said adhesive coating applied in a pattern to one side of said label sheet, substantially covering said label sheet except for the area defined by said hang strips, so that said hang strips are free of adhesive;*

*said label sheet having a top edge positioned nearer to the bottom end than to the open end and a bottom edge positioned nearer to the open end than to the bottom end of a container when adhered thereto;*

*said label sheet having a transverse axis corresponding with the circumference and a longitudinal axis corresponding with the height of a container when adhered thereto, said label sheet having a transverse middle;*

*each said hang strip folding along said integral end thereof and extending beyond the bottom end of a container a sufficient distance to enable said engageable ends to engage with a hook;*

*said integral end of one of said hang strips positioned near one of the sides of said label sheet, and said engageable end of the same said hang strip positioned toward said transverse middle of said label sheet; and*

*said integral end of the other said hang strip positioned at or near said transverse middle of said label sheet, and said engageable end of the same said hang strip positioned toward the other side of said label sheet.*

*38. A label hanger as claimed in claim 37 wherein each said hang strip has a top edge and a bottom edge;*

*said top edges nearer to the bottom end of a container and farther from the open end of the container than respective said bottom edges when said label assembly is adhered to the container;*

*said top edges shorter in length than respective said bottom edges by a distance substantially equal to the distance between said edges; and*

*each said integral end respectively extending between said top edge and said bottom edge;*

*whereby when said hang strips are extended and said engageable ends thereof are engaged with a hook, said integral ends are angled with respect to said transverse axis of said label sheet by approximately 45 degrees.*

*39. A label and backing sheet assembly for the application of hang strip type labels to containers comprising:*

*a backing strip layer coated with a release coating;*

*a label layer overlying said backing strip layer;*

*said label layer including a plurality of spaced individual labels, each said label including at least one hang strip having ties holding said hang strip in place on said label;*

*adhesive between each said label and said backing strip layer in the areas of said label other than said hang strip; and*

*the self-sustaining layers of said assembly consisting solely of said backing strip layer and said label layer;*

*whereby when said labels are applied to a container, said hang strips may be partly pulled loose from the balance of said label by breaking said ties, with the container being exposed in each area where a hang tab is pulled away from the container, and said hang strips permitting support of the container from said hang strips with the container inverted.*

* * * * *